United States Patent [19]

Das

[11] Patent Number: 4,591,603
[45] Date of Patent: May 27, 1986

[54] 7-OXABICYCLOHEPTANE SUBSTITUTED PROSTAGLANDIN ANALOGS USEFUL IN THE TREATMENT OF THROMBOTIC DISEASE

[75] Inventor: Jagabandhu Das, Plainsboro, N.J.

[73] Assignee: E. R. Squibb & Sons, Inc., Princeton, N.J.

[21] Appl. No.: 705,277

[22] Filed: Feb. 25, 1985

[51] Int. Cl.$^4$ .............. A61K 31/34; C07D 307/00
[52] U.S. Cl. ............................... 514/469; 549/463
[58] Field of Search ..................... 549/463; 514/469

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 0043292 8/1982 European Pat. Off. .
2039909 8/1980 United Kingdom .

Primary Examiner—Henry R. Jiles
Assistant Examiner—Bernard I. Dentz
Attorney, Agent, or Firm—Lawrence S. Levinson; Burton Rodney

[57] ABSTRACT

7-Oxabicycloheptane substituted prostaglandin analogs are provided having the structural formula

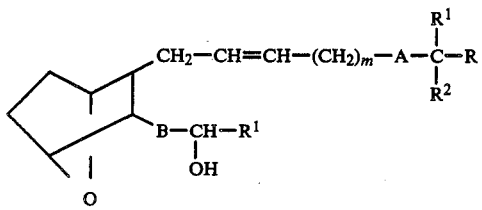

wherein A is O or S and R is $CH_2OH$,

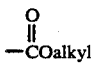

—COalkyl or $CO_2H$, and including all stereoisomers thereof.

The compounds are cardiovascular agents useful, for example, in the treatment of thrombotic disease.

10 Claims, No Drawings

7-OXABICYCLOHEPTANE SUBSTITUTED PROSTAGLANDIN ANALOGS USEFUL IN THE TREATMENT OF THROMBOTIC DISEASE

DESCRIPTION OF THE INVENTION

The present invention relates to 7-oxabicycloheptane substituted prostaglandin analogs which are cardiovascular agents useful, for example, in the treatment of thrombotic disease. These compounds have the structural formula

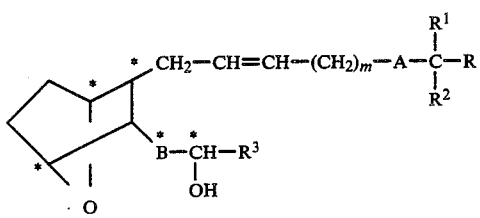

and including all stereoisomers thereof, wherein

A is sulfur or oxygen; m is 1 to 5; R is $CH_2OH$,

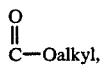

or $CO_2H$; B is $-CH=CH-$ or $-(CH_2)_2-$; $R^1$ and $R^2$ may be the same or different and are hydrogen or lower alkyl; and $R^3$ is lower alkyl, aryl, aralkyl, cycloalkyl, cycloalkylalkyl or lower alkenyl.

Thus, the compounds of formula I of the invention encompass two basic types of compounds which have the following structures:

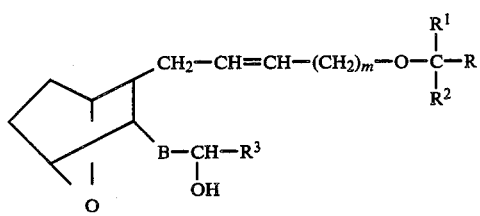

and

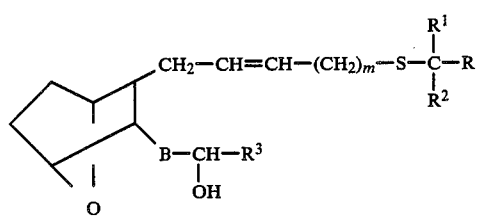

The term "lower alkyl" or "alkyl" as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent or an alkylcycloalkyl substituent.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or 1 or 2 lower alkoxy groups.

The term "aryl" or "Ar" as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, halogens (Cl, Br or F), and/or 1 or 2 lower alkoxy groups.

The term "aralkyl", "aryl-alkyl" or "aryl-lower alkyl" as used herein refers to lower alkyl groups as discussed above having an aryl substituent, such as benzyl.

The term "lower alkenyl" or "alkenyl" includes straight or branched chain radicals of from 2 to 12 carbons, preferably 2 to 6 carbons in the normal chain, which include one double bond in the normal chain, such as ethenyl, 2-propenyl, 3-butenyl, 2-butenyl, 1-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

Preferred are those compounds of formula I wherein A is O or S, and m is 1 or 2, B is $CH=CH$, R is $CH_2OH$,

or $CO_2H$, $R^1$ and $R^2$ are each H and $R^3$ is lower alkyl, aryl, such as phenyl, or aralkyl such as benzyl or benzylmethyl.

The various compounds of the invention may be prepared as outlined below.

The compounds of formula I of the invention may be prepared as described below.

The starting tetrahydropyranyl ether X may be prepared according to the following reaction sequence.

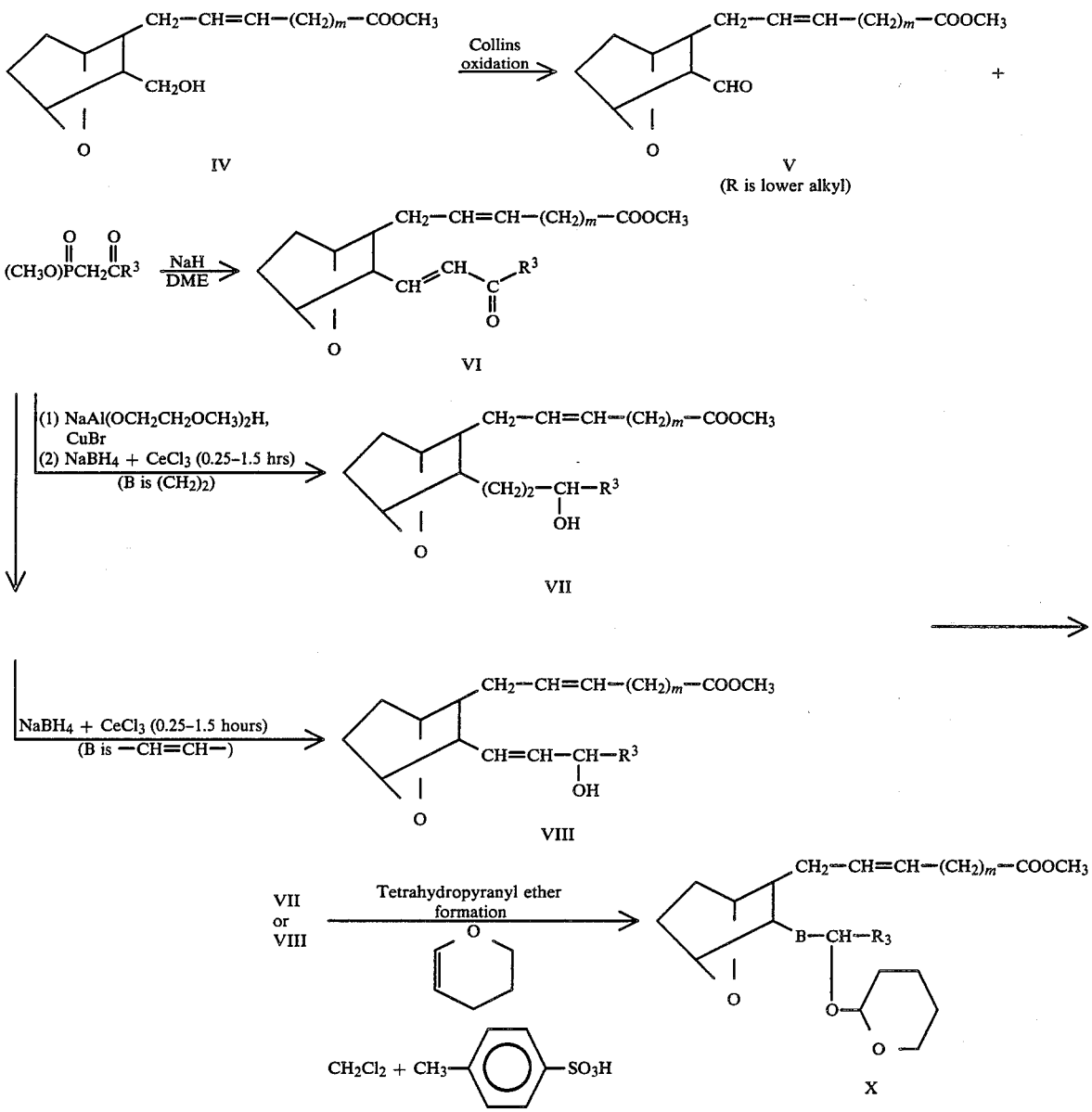

The starting lower alkyl ester containing the hydroxymethyl group (that is, compound IV) (prepared as described in U.S. Pat. No. 4,143,054) is used to form the aldehyde V. Thus, to form aldehyde V, compound IV is subjected to a Collins oxidation, for example, by reacting IV with chromium oxide in pyridine.

Aldehyde V of the structure

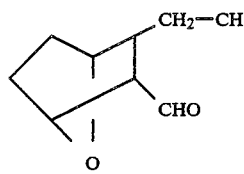

wherein R is lower alkyl is reacted with a dialkoxy phosphonate, such as of the structure

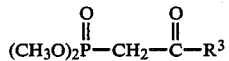

employing a molar ratio of V:A of within the range of from about 1:1 to about 0.5:1, under basic conditions, such as in the presence of sodium hydride or lithium diisopropylamide and an inert organic solvent, such as dimethoxyethane (DME), ether, tetrahydrofuran or toluene to form a compound of the structure

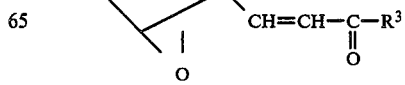

Compound VI may then be reduced by two different ways as outlined above to form compounds VII or VIII

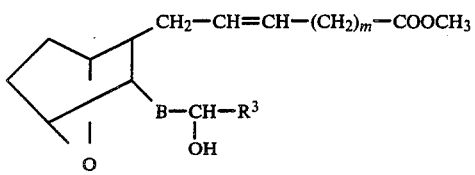

VII — B is (CH$_2$)$_2$
VIII — B is —CH=CH— or compounds of the general formula IX

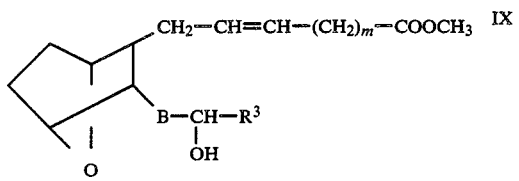

The allylic alcohol IX is made to undergo tetrahydropyranyl ether formation by reacting allylic alcohol IX with dihydropyran in the presence of an inert organic solvent such as methylene chloride or ether and catalytic amount of p-toluene sulfonic acid at reduced temperatures of from about 0° C. to about 10° C., to form the tetrahydropyranyl ether of formula X

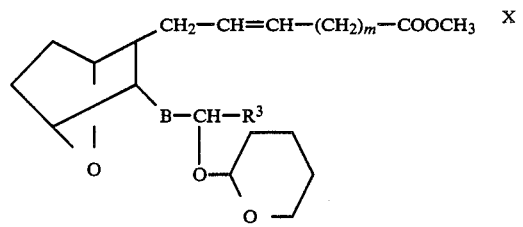

Compounds of the invention wherein R is CH$_2$OH, that is,

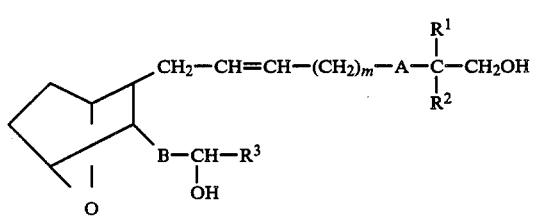

may be prepared by hydrolyzing tetrahydropyranyl ether X by treatment with a base such as lithium hydroxide, potassium carbonate or sodium hydroxide in the presence of an inert solvent such as tetrahydrofuran, methanol or dimethoxyethane-water to form the corresponding alkali metal salt which is then treated with acid such as HCl to form the acid compound XI

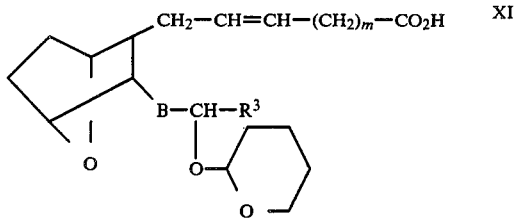

Acid XI is dissolved in an inert solvent such as tetrahydrofuran and water and is then treated with sodium bicarbonate and crystalline iodine to form the iodo-lactone XII

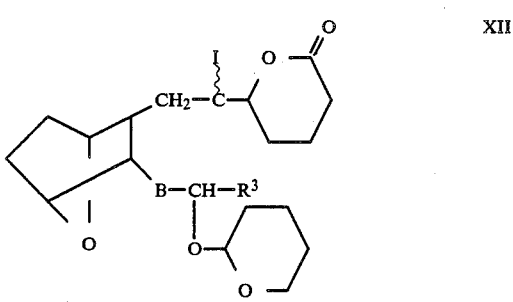

which is treated with methanol, then a base such as lithium hydroxide and then acidified by addition of HCl to form diol XIII

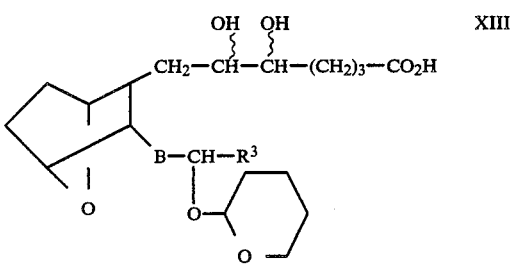

Diol XIII is treated with an ethereal solution of diazomethane to form diol XIV

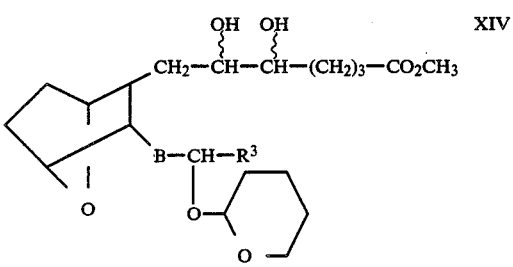

which is then treated with sodium meta-periodate in the presence of methanol to form aldehyde XV

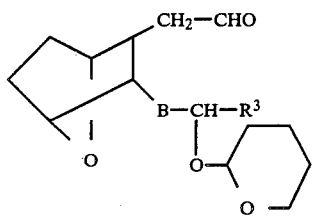

XV

Aldehyde XV is then reacted with carboxymethoxymethylene triphenyl phosphorane $(C_6H_5)_3P=CH-(CH_2)_{m-1}-CO_2CH_3$ in the presence of methanol to form ester XVI

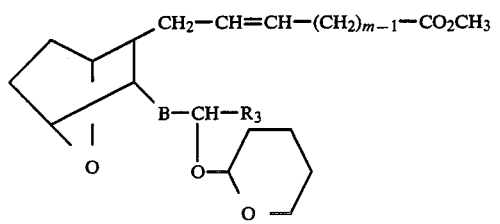

XVI which is treated with diisobutyl aluminum hydride in the presence of an inert solvent such as tetrahydrofuran at reduced temperatures of from about −70° to about −85° C. under an inert, such as argon, atmosphere, to form the hydroxymethyl compound XVII

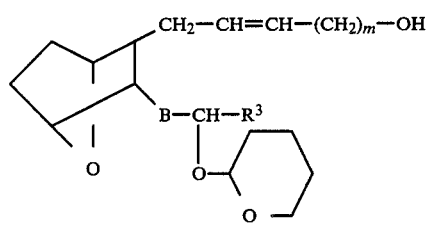

XVII

To form compounds of the invention where A is O, the hydroxymethyl compound XVII is dissolved in an inert solvent such as tetrahydrofuran and tetrahydropyranyl compound B

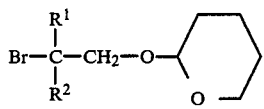

B and tetra n-butyl ammonium hydrogen sulfate and base such as sodium hydroxide are added to form the di-tetrahydropyran compound XVIII

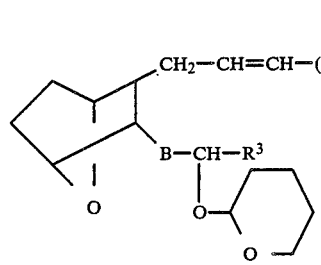

XVIII

Compound XVIII in methanol solution is then hydrolyzed by treatment with a strong acid such as HCl, Amberlyst resin or acetic acid to form alcohol IB

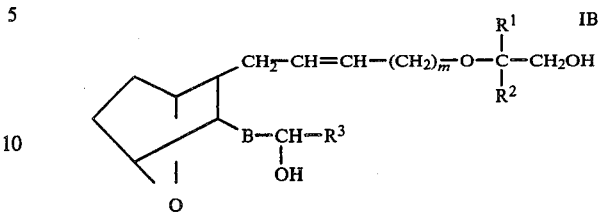

IB

Compounds of formula I wherein R is $CH_2OH$ and A is S, that is

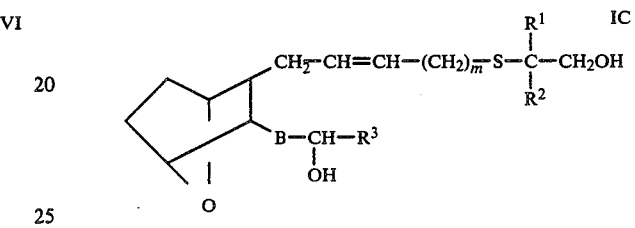

IC may be prepared by treating hydroxymethyl compound XVIII with the reaction product of triphenylphosphine and diisopropylazodicarboxylate and thiolacetic acid C

C in the presence of an inert solvent such as tetrahydrofuran to form the thioacetate XIX

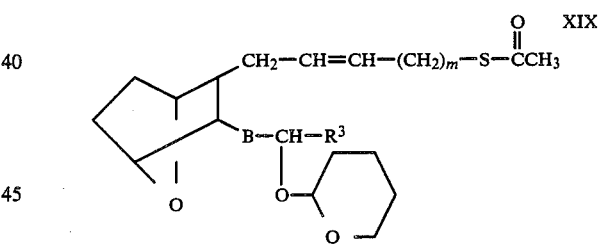

XIX which is reduced with lithium aluminum hydride in the presence of tetrahydrofuran or other inert solvent, and is then treated with tetrahydropyran B to form compound IC.

Compounds of the invention wherein R is

and A is O, that is

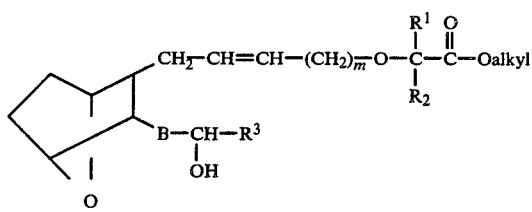

may be prepared as follows.

Hydroxymethyl compound XVII, that is

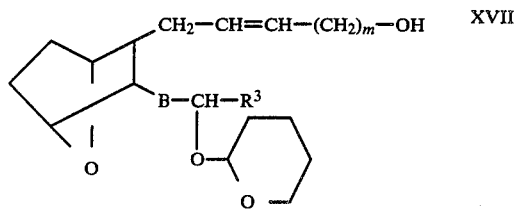

is mixed with an inert organic solvent such as tetrahydrofuran, acetonitrile or dimethylformamide and then treated with tetra n-butylammonium hydrogen sulfate, base such as sodium hydroxide and an ester of the structure

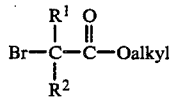

to form compound XX

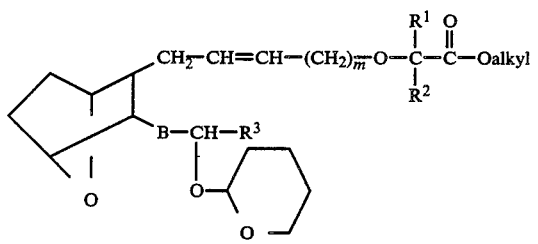

Compound XX in methanol solution is then treated with strong acid such as HCl, Amberlyst resin or acetic acid to form ID.

Compounds of formula I wherein R is

and A is S, that is

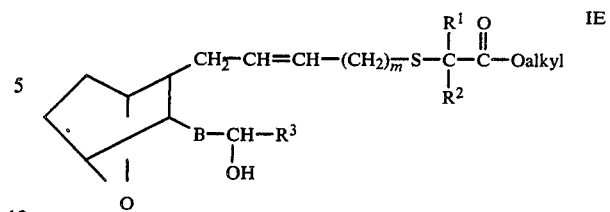

may be prepared by treating thiolacetate XIX, that is

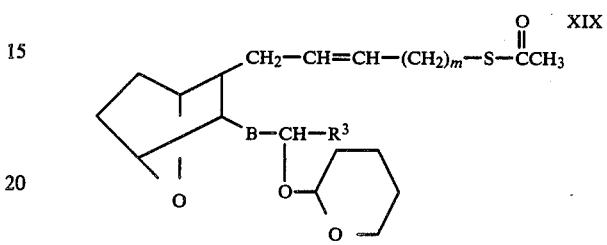

with lithium aluminum hydride or other reducing agent such as di-isobutylaluminum hydride or base such as potassium carbonate or sodium methoxide in an organic solvent such as tetrahydrofuran or methanol and ester D

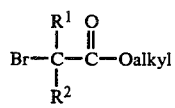

to form thioester XXI

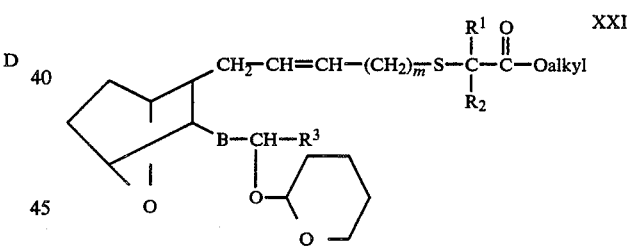

which is treated with strong acid such as HCl, acetic acid or Amberlyst resin in the presence of methanol to form IE.

Compounds of formula I wherein R is COOH, that is IF

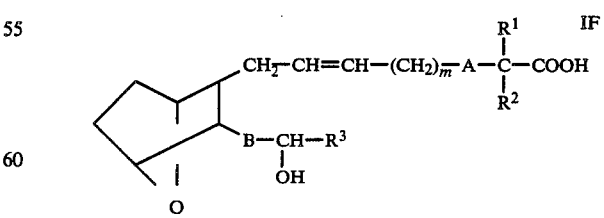

may be prepared by hydrolyzing ester ID or IE by treatment with a strong base such as sodium hydroxide or lithium hydroxide in the presence of an inert solvent such as tetrahydrofuran, methanol or dimethoxyethane-water to form the corresponding alkali metal salt which is then treated with strong acid such as HCl to form the acid compound of the invention IF.

The compounds of this invention have five centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

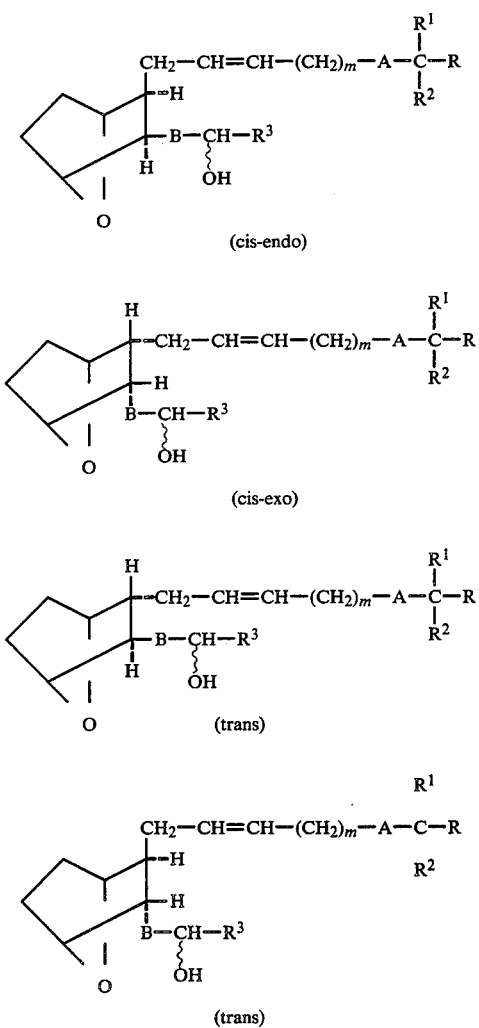

The wavy line (⌇) in the above formulae indicates that the hydroxy group in each of the compounds of formulae Ia–Id is either R($\beta$) or S($\alpha$).

The nucleus in each of the compounds of the invention is depicted as

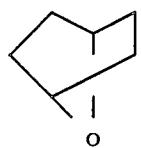

for matter of convenience; it will also be appreciated that the nucleus in the compounds of the invention may be depicted as

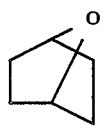

The compounds of this invention are cardiovascular agents useful as platelet aggregation inhibitors, such as inhibiting arachidonic acid-induced platelet aggregation (e.g., for treatment of thrombotic disease, such as coronary or cerebral thromboses) and in inhibiting bronchoconstriction as induced by asthma. They are also selective thromboxane $A_2$ receptor antagonists and synthetase inhibitors, e.g., having a vasodilatory effect for treatment of myocardial ischemic disease, such as angina pectoris.

The compounds of the invention can be administered orally or parenterally to various mammalian species known to be subject to such maladies, e.g., cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in degrees Centigrade.

EXAMPLE 1

[1S-[1α,2β(E),3β(1E,3R,4S),4α]]-2-[[4-[3-(3-Hydroxy-4-phenyl-1-pentenyl)-7-oxabicyclo[2.2.1]hept-2-yl]-2-butenyl]oxy]ethanol

A.

[1α,2β(Z),3β(1E),4α]-7-[3-(3-Hydroxy-4-phenyl-1-pentenyl)-7-oxabicyclo[2.2.1]hept-2-yl]-5-heptenoic acid, methyl ester (1) (+) Methyl 2-phenylpropionate (+) 2-Phenylpropionic acid (8.4 g, 56 mmol) in methanol (180 ml) and concentrated $H_2SO_4$ (2 ml) were heated at reflux for 4 hours. The reaction was cooled down to room temperature and concentrated in vacuo (~100 ml). The products were extracted with Et$_2$O (150 ml×3), which was washed with saturated NaHCO$_3$, H$_2$O and dried over MgSO$_4$. Filtration and evaporation of solvent yielded a yellow oil (8.9 g), which was distilled to give (+) methyl 2-phenylpropionate as a colorless oil (8.34 g, 51 mmol, 91%, b.p. 73° C./1.5 mm Hg), $[\alpha]^D = +111°$ (c=2, toluene).

(2) (+) 2-Oxo-3-phenylbutyl dimethyl phosphonate n-Butyllithium (1.6 M, 62.5 ml, 100 mmol) was added dropwise to a magnetically stirred solution of dimethylmethyl phosphonate (12.4 g, 100 mmol) in THF (90 ml) at −78° C. Stirring was continued for 30 minutes at −78° C. Then ester from Part A (8.2 g, 50 mmol) was added dropwise to give a yellow colored solution. After 3 hours stirring at −78° C., the reaction was warmed to room temperature and stirred for 1 hour. The reaction was quenched by addition of acetic acid to pH 5~6. The solvent was removed in vacuo and H$_2$O (100 ml) was added. The products were extracted with CH$_2$Cl$_2$ (100 ml×3), which was washed with saturated NaHCO$_3$, H$_2$O and dried over MgSO$_4$. Filtration and evaporation of solvent left a yellow oil. This was fractionated to give (+)2-oxo-3-phenylbutyl dimethyl phosphonate (8.1 g, 31.6 mmol, 63%, b.p. 142°–144°/0.2 mm Hg), $[\alpha]^D = +235°$ (c=2, toluene).

(3) [1α,2β(Z),3β(1E,4S),4α]-7-[3-(3-Oxo-4-phenyl-1-pentenyl)-7-oxabicyclo[2.2.1]hept-2-yl]-5-heptenoic acid, methyl ester.

Sodium hydride (201 mg of 50% in mineral oil, 4.18 mmol) was suspended in distilled dimethoxyethane (70 ml) in an argon atmosphere and treated with a solution of Part A(2) phosphonate (1.45 g, 4.7 mmol) in DME (10 ml). The mixture was stirred at room temperature 90 minutes. A solution of (+)-[1α,2β(Z),3β,4α[-7-[3-formyl-7-oxabicyclo[2.2.1]hept-2-yl]-5-heptenoic acid, methyl ester (prepared as described in U.S. Pat. No. 4,143,054) (1.031 g, 3.8 mmol) in DME (5 ml) was then added and the mixture was stirred overnight at room temperature. The reaction was quenched by adding glacial acetic acid (0.5 ml) and the solvent was removed in vacuo. Ether and saturated NaHCO$_3$ were added and the layers were separated. The ether layer was washed once with saturated NaHCO$_3$ solution, dried over MgSO$_4$, filtered and taken to dryness in vacuo leaving a viscous oil. This was chromatographed on silica gel 60 (110 g), eluting with ether-pet ether (2:3) to give 992 mg (66%) of title A (3) compound as an oil. A faster moving material (98 mg, 6.5%) was also isolated and identified by $^1$H NMR as the cis double bond isomer.

(4) [1α,2β(Z),3β(1E),4α]-7-[3-(3-Hydroxy-4-phenyl-1-pentenyl)-7-oxabicyclo[2.2.1]hept-2-yl]-5-heptenoic acid, methyl ester Title compound from Part A (3) (0.99 g, 2.49 mmol) and CeCl$_3$~7.6H$_2$O (0.954 g, 2.49 mmol) were dissolved in methanol (25 ml) and THF (2 ml). The solution was cooled in an ice bath and NaBH$_4$ (94.1 mg, 2.5 mmol) was added portionwise in 30 seconds. The ice bath was removed and the mixture was stirred 10 minutes, then poured into saturated NH$_4$Cl solution (200 ml). The product was extracted into ethyl acetate (5×50 ml). The combined ethyl acetate extracts were dried (MgSO$_4$), filtered, and freed of solvent in vacuo to give a viscous oil (0.953 g). This was chromatographed on silica gel 60 (60 g) eluting with ether-pet ether (3:2) to give 616 mg of nearly clean faster moving isomer and 150 mg (15%) of slower moving isomer. TLC's silica gel; Et$_2$O-pet ether 3:2; vanillin R$_f$'s 0.35 and 0.25. The faster moving isomer was rechromatographed eluting with the same solvent to give 605 mg (61%) of title A compound.

B.
[1α,2β(Z),3β(1E,4S),4α]-7-[3-(3-Tetrahydropyranyloxy-4-phenyl-1-pentenyl)-7-oxabicyclo[2.2.1]hept-2-yl]-5-heptenoic acid, methyl ester To a solution of 2.16 g of title A chiral allylic alcohol (5.4 mmole) in 20 ml of dry methylene chloride was added with stirring a catalytic amount of p-toluene sulfonic acid, followed by 750 μl of dihydropyran (8.33 mmole) at 0°–5° C. The reaction mixture was stirred at 0°–5° C. for 40 minutes whereupon it was washed with aqueous sodium bicarbonate solution. The methylene chloride layer was separated and the aqueous layer was extracted with ether. The combined organic extract was dried over anhydrous magnesium sulfate and concentrated under reduced pressure. Purification by flash chromatography on a silica gel column gave 2.43 g of desired title THP-ether (eluting solvent 10–15% ethyl acetate in hexane).

C.
[1α,2β(Z),3β(1E,4S),4α]-7-[3-(3-Tetrahydropyranyloxy-4-phenyl-1-pentenyl)-7-oxabicyclo[2.2.1]hept-2-yl]-5-heptenoic acid To a solution of 11.78 g of Part B tetrahydropyranyl ester (24.3 mmole) in 100 ml of distilled THF (tetrahydrofuran) was added with stirring 50 ml of a 1N aqueous lithium hydroxide solution (50 mmole). The reaction mixture was allowed to stir at room temperature under an argon atmosphere for 24 hours, whereupon it was placed in an ice-water bath and carefully acidified to pH 4.5 by dropwise addition of a 1N aqueous hydrochloric acid solution. The THF layer was separated and the aqueous layer was extracted several times with ether. The combined ether and THF extract was washed with saturated salt solution, dried over anhydrous magnesium sulfate and finally was concentrated under reduced pressure to obtain 11.27 g of desired title acid as a colorless viscous oil.

D.
(1α,2β,3β,4α)-7-[3-(3-Tetrahydropyranyloxy-4-phenyl-1-pentenyl)-7-oxabicyclo[2.2.1]hept-2-yl]-6-iodo-5-hydroxypentanoic acid, δ-lactone To a solution of 8.47 g of Part C tetrahydropyranyl carboxylic acid (18 mmole) in 180 ml of distilled THF and 90 ml of water, placed in a R. B. flask wrapped with an aluminum foil was added with vigorous stirring 17.4 g of solid sodium bicarbonate (210 mmol). The reaction mixture was placed in an ice-water bath (maintained at 0°–5° C. by occasional addition of fresh ice) and a solution of 6.86 g of crystalline iodine (27 mmole, 1.5 equiv) in 20 ml of dry THF was added. The reaction mixture was stirred vigorously at 0°–5° C. for 24 hours, whereupon it was poured into 500 ml of an aqueous sodium bisulfite solution. The THF layer was separated and the aqueous layer was reextracted several times with ether. The combined organic extract was dried over anhydrous magnesium sulfate and finally was concentrated under reduced pressure to obtain 10.25 g of crude title iodolactone as a light yellow viscous oil. The crude title iodo-lactone was used for the next reaction without any purifications.

E.
(1α,2β,3β,4α)-7-[3-(3-Tetrahydropyranyloxy-4-phenyl-1-pentenyl)-7-oxabicyclo[2.2.1]hept-2-yl]-5,6-dihydroxyheptanoic acid and

F.
(1α,2β,3β,4α)-7-[3-(3-Tetrahydropyranyloxy-4-phenyl-1-pentenyl)-7-oxabicyclo[2.2.1]hept-2-yl]-5,6-dihydroxyheptanoic acid, methyl ester To a solution of 10.25 g of crude Part D iodo-lactone from the previous reaction was added with stirring 180 ml of absolute methanol. Within a few minutes, a precipitate was obtained. TLC also indicated the appearance of two new high $R_f$ spots (presumably the epoxy esters). 90 ml of a 1N aqueous lithium hydroxide solution was added to the reaction mixture and stirring was continued at room temperature for 24 hours. The reaction mixture was now placed in an ice-water bath and it was carefully acidified to pH 4.5 by slow addition of a 2N aqueous hydrochloric acid solution. The reaction mixture was now extracted with methylene chloride (X3) and finally with ether (X3). The combined organic extract was washed with saturated brine, dried over anhydrous magnesium sulfate and finally was concentrated in vacuo to obtain acid compound E as a viscous oil. The oily residue was dissolved in 100 ml of dry ether and an ethereal solution of diazomethane was added to the reaction mixture until the yellow color persisted. After 30 minutes, argon was passed through the reaction mixture to remove excess diazomethane. The reaction mixture was now concentrated under reduced pressure and the crude residue was chromatographed on a silica column. Elution with 30% ethyl acetate in hexane, followed by 50% ethyl acetate in hexane and finally with ethyl acetate afforded 6.93 g of desired title F diol as a white crystalline solid.

G.
(1α,2β,3β,4α)-2-[3-(3-Tetrahydropyranyloxy-4-phenyl-1-pentenyl)-7-oxabicyclo[2.2.1]hept-2-yl]acetaldehyde To 1.0 g of Part F diol (1.9 mmole) in 20 ml of methanol at 25° C. was added a solution of 1.0 g of sodium metaperiodate (4.6 mmole, 2.5 equiv) in 5 ml of $H_2O$. After stirring at 25° C. for 2 hours, the reaction mixture was extracted with three 20 ml portions of methylene chloride. The organic layer was dried over anhydrous $MgSO_4$ and concentrated to give crude title aldehyde as an oil. This aldehyde was used directly in the next reaction.

H.
1α,2β(2Z),3β,4α]-4-[3-(3-Tetrahydropyranyloxy-4-phenyl-1-pentenyl)-7-oxabicyclo[2.2.1]hept-2-yl]-2-butenoic acid, methyl ester and

I.
[1α,2β(2E),3β,4α]-4-[3-(3-Tetrahydropyranyloxy-4-phenyl-1-pentenyl)-7-oxabicyclo[2.2.1]hept-2-yl]-2-butenoic acid, methyl ester To a solution of 1.15 g of Part G aldehyde (3 mmole) in 25 ml of dry methanol was added with stirring 1.77 g of crystalline carbomethoxymethylenetriphenylphosphorane (5 mmole). After stirring at room temperature for 5 hours, methanol was removed by distillation under reduced pressure. The crude residue was triturated with ether, cooled in an ice-water bath and filtered. The residue was washed with hexane. The filtrate was concentrated under reduced pressure and chromatographed on a 200 g silica gel column. Graded elution with 5% ethyl acetate in hexane followed by 7% ethyl acetate in hexane and finally with 10% ethyl acetate in hexane gave 420 mg of pure desired Z-ester (title H), 300 mg of a roughly 1:1 mixture of E:Z ester and 410 mg of pure E-ester (title I). From p.m.r. spectrum, the ratio of E:Z ester was calculated to be ~1:1. Total yield=86%.

J.
[1α,2β(2E),3β,4α]-4-[3-(3-Tetrahydropyranyloxy-4-phenyl-1-pentenyl)-7-oxabicyclo[2.2.1]hept-2-yl]-2-butenol To a solution of 946 mg of E-ester (Part I) (2.1 mmole) in 15 ml of dry tetrahydrofuran at −78° C. under an argon atmosphere was added dropwise 4.21 ml of a 1.5 M solution of diisobutylaluminumhydride in toluene (6.4 mmole, 3 equiv.). After stirring at −78° C. for 2 hours, the reaction was quenched with a saturated solution of ammonium chloride. The mixture was stirred at 25° C. for 30 minutes, then the layers were separated. The aqueous layer was extracted with four 30 ml portions of $CH_2Cl_2$. The combined organic layer was dried over anhydrous $MgSO_4$ and filtered through a bed of Celite. The filtrate was concentrated to give 760 mg of title alcohol as an oil. This was used in the next reaction without further purification.

K.
[1S-[1α,2β(E),3β,4α]-2-[[4-[3-(3-Tetrahydropyranyloxy-4-phenyl-1-pentenyl)-7-oxabicyclo[2.2.1]hept-2-yl]-2-butenyl]oxy]ethanol, tetrahydropyranyl ether To a solution of 356 mg of Part J alcohol (0.85 mmole) in 3.8 ml of THF was added 1.8 g of 1-[2-bromoethoxy] tetrahydropyran (8.5 mmole, 10 equiv.), 295 mg of tetra n-butylammonium hydrogen sulfate (0.85 mmole, 1 equiv.) and 3.8 ml of a 50% aqueous sodium hydroxide. After stirring at 25° C. for 2 days, the reaction mixture was diluted with 100 ml of ether and washed with three 15 ml portions of $H_2O$. The organic layer was dried over anhydrous $MgSO_4$ and concentrated.

The residue was purified on a silica gel column with 500 ml of 20% EtOAc/hexanes, 500 ml of 30% EtOAc/hexanes and 500 ml of 40% EtOAc/hexanes to give 320 mg of title compound as an oil.

L.
[1S-[1α,2β(E),3β(1E,3R,4S),4α]]-2-[[4-[3-(3-Hydroxy-4-phenyl-1-pentenyl)-7-oxabicyclo[2.2.1]hept-2-yl]-2-butenyl]oxy]ethanol To a solution of 320 mg of Part K compound in 3 ml of methanol at 25° C. was added 320 mg of Amberlyst-15 resin. After stirring at 25° C. for 20 hours, the mixture was diluted with 30 ml of ether and filtered. The filtrate was concentrated to give 203 mg of an oil.

Purification was done on a silica gel column, with 50% EtOAc/hexanes as eluting solvents, to yield 175 mg of title product as a clear oil.

TLC: Silica gel; EtOAc; $R_f$~0.5

Anal Calcd for $C_{23}H_{32}O_4 \cdot 0.5\ H_2O$: C, 72.38; H, 8.72. Found: C, 72.38; H, 8.63. $[\alpha]_D = +42°$, c=5.3 mg/ml MeOH

EXAMPLE 2

[1S-[1α,2β(Z),3β(1E,3R,4S,4α]]-[[4-[3-(3-Hydroxy-4-phenyl-1-pentenyl)-7-oxabicyclo[2.2.1]hept-2-yl]-2-butenyl]oxy]acetic acid, t-butyl ester

A.

[1α,2β(Z),3β(1E,3R,4S),4α]-4-[3-(3-Tetrahydropyranyloxy-4-phenyl-1-pentenyl)-7-oxabicyclo[2.2.1]hept-2-yl]-2-butenol To a solution of 442 mg of Example 1, Part H ester (1.0 mmole) in 5 ml of dry THF was added slowly 2 ml of a 1.5 M solution of diisobutylaluminum hydride in toluene (3 mmole, 3 equiv.) at −78° C. under an argon atmosphere. After stirring at −78° C. for 2 hours, the reaction was quenched by slow addition of an excess amount of acetone at −78° C. The mixture was warmed to 25° C. and 3.0 g of silica gel was added along with 1 drop of glacial acetic acid. After stirring at 40° C. for 1 hour, the mixture was filtered. The filtrate was concentrated to give 388 mg of title alcohol as a clear oil.

B.

[1S-[1α,2β(Z),3β(1E,3R,4S),4α]]-[[4-[3-(3-Tetrahydropyranyloxy-4-phenyl-1-pentenyl)-7-oxabicyclo[2.2.1]hept-2-yl]-2-butenyl]oxy]acetic acid, t-butyl ester To a mixture of 388 mg of Part A alcohol (0.94 mmole) in 5.5 ml of THF at 25° C. was added 500 mg of tetra n-butylammonium hydrogen sulfate (1.64 mm, 1.5 equiv.), 5.5 ml of 50% sodium hydroxide, and 1.8 g of t-butyl bromoacetate (9.4 mmole, 10 equiv.). After stirring at 25° C. for 5 hours, the mixture was diluted with 100 ml of ether and washed with three 20 ml portions of H₂O. The organic layer was dried over anhydrous MgSO₄ and concentrated. The residue was purified on a silica gel column with 10% EtOAc/hexanes as eluting solvents, to give 335 mg of title ester as an oil.

C.

[1S-[1α,2β(Z),3β(1E,3R,4S),4α]]-[[4-[3-(3-Hydroxy-4-phenyl-1-pentenyl)-7-oxabicyclo[2.2.1]hept-2-yl]-2-butenyl]oxy]acetic acid, t-butyl ester A mixture of 335 mg of Part B ester (0.63 mmole) and 300 mg of Amberlyst-15 resin in 3 ml of methanol was stirred at 25° C. for 20 hours, then diluted with 30 ml of ether and filtered through a bed of Celite. The filtrate was concentrated. The residue was purified on a silica gel column, with 20% EtOAc/hexanes as eluting solvents, to give 196 mg of title ester product as an oil.

EXAMPLE 3

[1S-[1α,2β(Z),3β(1E,3R,4S),4α]]-[[4-[3-(3-Hydroxy-4-phenyl-1-pentenyl)-7-oxabicyclo[2.2.1]hept-2-yl]-2-butenyl]oxy]acetic acid To a solution of 196 mg of Example 2 ester (0.44 mmole) in 2 ml of THF at 25° C. was added 2 ml of 50% sodium hydroxide. After stirring at 25° C. for 20 hours, the mixture was concentrated. The residue was diluted with 5 ml of H₂O, then extracted with two 10 ml portions of ether. The aqueous layer was acidified with concentrated HCl and extracted with four 15 ml portions of CH₂Cl₂. The organic layer was dried over anhydrous MgSO₄ and concentrated to give 140 mg of title acid product as a clear oil.

TLC: Silica gel: 10% MeOH/CH₂Cl₂+1 drop AcOH; $R_f$~0.5

Anal Calcd for $C_{23}H_{30}O_5$, 0.5 H₂O: C, 69.85; H, 7.90. Found: C, 69.94; H, 7.92. $[\alpha]_D = +78.5°$, c=2.0 mg/ml MeOH

EXAMPLE 4

[1S-[1α,2β(E),3β(1E,3R,4S),4α]]-[[4-[3-(3-Hydroxy-4-phenyl-1-pentenyl)-7-oxabicyclo[2.2.1]hept-2-yl]-2-butenyl]oxy]acetic acid, methyl ester

A.

[1S-[1α,2β(E),3β(1E,3R,4S),4α]]-[[4-[3-(3-Tetrahydropyranyloxy-4-phenyl-1-pentenyl)-7-oxabicyclo[2.2.1]hept-2-yl]-2-butenyl]oxy]acetic acid To a mixture of 280 mg of Example 1, Part I alcohol (0.67 mmole) in 4 ml of THF at 25° C. was added 336 mg of tetra-n-butylammonium hydrogensulfate (0.96 mmole, 1.4 eq., 4 ml of 50% sodium hydroxide, and 1.7 g of t-butylbromoacetate (8.3 mmole, 12.5 eq.). After stirring at 25° C. for 20 hours, the reaction mixture was concentrated. The residue was diluted with 10 ml of H₂O and extracted with two 15 ml portions of ether. The aqueous layer was acidified to pH 3 with concentrated HCl, then extracted with five 20 ml portions of CH₂Cl₂. The organic layer was dried over anhydrous MgSO₄ and concentrated. The residue was triturated with 20 ml of ether, and the solution was filtered. The filtrate was concentrated to give 100 mg of title acid as an oil. This was used directly in the next reaction without further purification.

B.

[1S-[1α,2β(E),3β(1E,3R,4S),4α]]-[[4-[3-(3-Hydroxy-4-phenyl-1-pentenyl)-7-oxabicyclo[2.2.1]hept-2-yl]-2-butenyl]oxy]acetic acid, methyl ester A mixture of 100 mg of Part A acid (0.2 mm), and 100 mg of Amberlyst-15 resin in 5 ml of methanol was stirred at 25° C. for 20 hours, then diluted with 30 ml of ether. The mixture was then filtered through a bed of Celite and the filtrate was concentrated. The residue was purified on a silica gel column. Elution with 200 ml of 20% EtOAc/hexanes, 300 ml of 40% EtOAc/hexanes gave 60 mg of title ester as an oil.

EXAMPLE 5

Q8

1S-[1α,2β(E),3β(1E,3R,4S),4α]]-[4-[3-(3-Hydroxy-4-phenyl-1-pentenyl)-7-oxabicyclo[2.2.1]hept-2-yl]-2-butenyl]oxy]acetic acid To a solution of 60 mg of Example 4 ester (0.15 mmole) in 2 ml of THF was added at 25° C. 500 μl of a 1N lithium hydroxide solution (0.5 mmole, 3.3 eq.). After stirring at 25° C. for 30 minutes, the reaction mixture was concentrated. The residue was diluted with 5 ml of H₂O and extracted with two 10 ml portions of ether. The aqueous layer was acidified with a saturated oxalic acid solution, then extracted with five 10 ml portions of CH₂Cl₂. The organic layer was dried over anhydrous MgSO₄ and concentrated to give 55 mg of title acid as an oil.

TLC: silica gel, 10% MeOH/CH₂Cl₂+1 drop AcOH; $R_f$~0.45.

Anal Calcd for $C_{23}H_{30}O_5$,0.33H₂O: C, 70.39; H, 7.88. Found: C, 70.39; H, 7.95. $[\alpha]_D = +38.1°$; c=3.2 mg/ml MeOH

EXAMPLE 6

[1S-[1α,2β(Z),3β(1E,3R,4S),4α]]-[[4-[3-(3-Hydroxy-4-phenyl-1-pentenyl)-7-oxabicyclo[2.2.1]hept-2-yl]-2-butenyl]thio]ace tic acid, methyl ester

A.
[1S-[1α,2β(Z),3β(1E,3R,4S),4α]]-4-[3-(3-Tetrahydropyranyl-4-phenyl-1-pentenyl)-7-oxabicyclo[2.2.1]hept-2-y]-2-butenethiol acetate To a solution of 420 mg of triphenylphosphine (1.6 mmole) in 5 ml of freshly distilled THF was added with stirring at 0° C., 340 mg of a 97% pure diisopropylazodicarboxylate over a period of 10 minutes. After stirring for additional 30 minutes at 0° C., a solution of 335 mg of Example 2 Part A allylic alcohol (0.8 mmol) and 140 μl of distilled thiolacetic acid (1.75 mmole) in 2 ml of dry THF was added dropwise over a period of 5 minutes. The reaction mixture was stirred at 0°–5° C. for 1 hour, whereupon it was concentrated under reduced pressure. The crude residue was triturated with ether and the precipitated phosphorus salts were filtered off. The filtrate was concentrated and chromatographed on a silica gel column. Elution with 5–30% ethyl acetate in hexane gave 293 mg of desired title thioacetate 77% yield).

B.
[1S-[1α,2β(Z),3β(1E,3R,4S),4α]]-[[4-[3-(3-Tetrahydropyranyloxy-4-phenyl-1-pentenyl)-7-oxabicyclo[2.2.1]hept-2-yl]-2-butenyl]thio]acetic acid, methyl ester To a suspension of 50 mg of 95% pure lithium aluminum hydride in 5 ml of freshly distilled THF was added with stirring at 0°–5° C., a solution of 293 mg of Part A thioacetate (0.61 mmole) in 2 ml of dry THF. After stirring for 1 hour at 0°–5° C., excess hydride reagent was decomposed by slow addition of saturated sodium sulfate solution. Precipitated inorganic salts were filtered through anhydrous magnesium sulfate. The filtrate was concentrated under reduced pressure and finally in vacuo to obtain the crude thiol. Crude thiol was dissolved in 5 ml of dry acetone and 300 mg of powdered potassium carbonate was added with stirring, followed by 450 mg of neat methylbromoacetate (3 mmol). After stirring at 0°–5° C. for 1 hour, the reaction mixture was diluted with ether and washed with water. The ether extract was dried over anhydrous magnesium sulfate, filtered and finally was concentrated under reduced pressure. The crude residue was chromatographed on a silica gel column and eluted with 5–25% ethyl acetate in hexane to obtain 155 mg of title 3-thia ester in 50% overall yield in two steps.

C.
[1S-[1α,2β(Z),3β(1E,3R,4S),4α]]-[[4-[3-(3-Hydroxy-4-phenyl-1-pentenyl)-7-oxabicyclo[2.2.1]hept-2-yl]-2-butenyl]thio]acetic acid, methyl ester To a solution of 155 mg of Part B 3-thia ester in 5 ml of dry methanol was added with stirring 50 mg of powdered and dry Amberlyst-15 acidic resin. After stirring at room temperature for 6 hours under an argon atmosphere, the reaction mixture was diluted with 50 ml of ether and filtered through a pad of anhydrous magnesium sulfate. The filtrate was thoroughly washed with aqueous sodium bicarbonate solution. The aqueous layer was extracted with ether (X2). The combined ether extract was dried over anhydrous magnesium sulfate and finally was concentrated under reduced pressure. Chromatography of the crude residue on a silica gel column, pretreated with 1% triethylamine and eluted with 20–50% ethyl acetate in hexane gave 125 mg of title thia ester product as a colorless oil.

Anal Calcd for $C_{24}H_{32}O_4S$, 0.25 mmoles of $H_2O$: C, 68.46, H, 7.78; S, 7.61. Found: C, 68.54; H, 7.77; S, 7.73.

EXAMPLE 7

[1S-[1α,2β(E),3β(1E,3R,4S),4α]]-2-[[4-[3-(3-Hydroxy-3-phenyl-1-propenyl)-7-oxabicyclo[2.2.1]hept-2-yl]-2-butenyl]oxy]ethanol Following the procedure of Example 1 except substituting propionic acid for 2-phenylpropionic acid, the title compound is obtained.

EXAMPLE 8

[1S-[1α,2β(E),3β(1E,3R,4S),4α]]-2-[[4-[3-(3-Hydroxy-4-phenyl-1-butenyl)-7-oxabicyclo[2.2.1]hept-2-yl]-2-butenyl]oxy]ethanol Following the procedure of Example 1 except substituting phenylacetic acid for 2-phenylpropionic acid, the title compound is obtained.

EXAMPLE 9

[1S-[1α,2β(E),3β(1E,3R,4S),4α]]-2-[[4-[3-(3-Hydroxy-3-cyclohexyl-1-propenyl)-7-oxabicyclo[2.2.1]hept-2-yl]-2-butenyl 9 oxy]ethanol Following the procedure of Example 1 except substituting cyclohexyl carboxylic acid for 2-phenylpropionic acid, the title compound is obtained.

EXAMPLE 10

[1S-[1α,2β(E),3β(1E,3R,4S),4α]]-2-[[4-[3-(3-Hydroxy-4-cyclopentyl-1-butenyl)-7-oxabicyclo[2.2.1]hept-2-yl]-2-butenyl]oxy]ethanol Following the procedure of Example 1 except substituting cyclopentylacetic acid for 2-phenylpropionic acid, the title compound is obtained.

EXAMPLE 11

[1S-[1α,2β(E),3β(1E,3R,4S),4α]]-2-[[4-[3-(3-Hydroxy-1,5-hexadienyl)-7-oxabicyclo[2.2.1]hept-2-yl]-2-butenyl]oxy]ethanol Following the procedure of Example 1 except substituting 2-propenyl carboxylic acid for 2-phenylpropionic acid, the title compound is obtained.

EXAMPLE 12

[1S-[1α,2β(E),3β(1E,3R,4S),4α]]-2-[[4-[3-(3-Hydroxy-1-nonenyl)-7-oxabicyclo[2.2.1]hept-2-yl]-2-butenyl]oxy]ethanol Following the procedure of Example 1 except substituting hexane carboxylic acid for 2-phenylpropionic acid, the title compound is obtained.

EXAMPLE 13

[1S-[1α,2β(E),3β(1E,3R,4S),4α]]-2-[[4-[3-(3-Hydroxy-1-pentenyl)-7-oxabicyclo[2.2.1]hept-2-yl]-2-butenyl]oxy]ethanol Following the procedure of Example 1 except substituting propionic acid for 2-phenylpropionic acid, the title compound is obtained.

EXAMPLE 14

[1S-[1α,2β(Z),3β(1E,3R,4S),4α]]-2-[[4-[3-(3-Hydroxy-4-phenyl-1-pentenyl)-7-oxabicyclo[2.2.1]hept-2-yl]-2-butenyl]thio]ethanol To a suspension of 114 mg lithium aluminum hydride (3 mmole) in 10 ml of dry THF, cooled in an ice-water bath is added dropwise a solution of 82 mg Example 6, Part C methyl ester (2 mmole) in 5 ml of dry THF. The reaction mixture is stirred at 0° C.→RT overnight, whereupon excess hydride reagent is destroyed by dropwise addition of saturated sodium sulfate solution; all the inorganic salts are precipitated as white granular solids. The reaction mixture is now filtered through anhydrous magnesium sulfate, and concentrated under reduced pressure to obtain Example 14 alcohol.

EXAMPLE 15

[1S-[1α,2β(E),3β(1E,3R,4S),4α]]-2-[[4-[3-(3-Hydroxy-3-phenyl-1-propenyl)-7-oxabicyclo[2.2.1]hept-2-yl]-2-butenyl]thio]ethanol Following the procedure of Examples 1 and 14 except substituting benzoic acid for 2-phenylpropionic acid, the title compound is obtained.

EXAMPLE 16

[1S-[1α,2β(E),3β(1E,3R,4S),4α]]-2-[[4-[3-(3-Hydroxy-3-cyclohexyl-1-propenyl)-7-oxabicyclo[2.2.1]hept-2-yl]-2-butenyl]thio]ethanol Following the procedure of Examples 1 and 14 except substituting cyclohexylcarboxylic acid for 2-phenylpropionic acid, the title compound is obtained.

EXAMPLE 17

[1S-[1α,2β(E),3β(1E,3R,4S),4α]]-2-[[4-[3-(3-Hydroxy-3-cycloheptyl-1-propenyl)-7-oxabicyclo[2.2.1]hept-2-yl]-2-butenyl]thio]ethanol Following the procedure of Examples 1 and 14 except substituting cycloheptyl carboxylic acid for 2-phenylpropionic acid, the title compound is obtained.

EXAMPLE 18

[1S-[1α,2β(E),3β(1E,3R,4S),4α]]-2-[[4-[3-(3-Hydroxy-4-cyclopentyl-1-butenyl)-7-oxabicyclo[2.2.1]hept-2-yl]-2-butenyl]thio]ethanol Following the procedure of Examples 1 and 14 except substituting cyclopentylacetic acid for 2-phenylpropionic acid, the title compound is obtained.

EXAMPLE 19

[1S-[1α,2β(E),3β(1E,3R,4S),-4α]]-2-[[4-[3-(3-Hydroxy-1,6-heptadienyl)-7-oxabicyclo[2.2.1]hept-2-yl]-2-butenyl]thio]ethanol Following the procedure of Examples 1 and 14 except substituting 3-butenyl carboxylic acid for 2-phenylpropionic acid, the title compound is obtained.

EXAMPLE 20

[1S-[1α,2β(E),3β(1E,3R,4S),4α]]-2-[[4-[3-(3Hydroxy-1-hexenyl)-7-oxabicyclo[2.2.1]hept-2-yl]-2-butenyl]thio]ethanol Following the procedure of Examples 1 and 14 except substituting propionic acid for 2-phenylpropionic acid, the title compound is obtained.

EXAMPLE 21

[11α,2β(5Z),3β(3R,4S),4α]-2-[[4-[3-(3-Hydroxy-4-phenyl-1-pentyl)-7-oxabicyclo[2.2.1]hept-2-yl]2-butenyl]oxy]ethanol

A.

[1S-[1α,2β(Z),3β(4S),4α]]-7-[3-(3-Oxo-4-phenyl-1-pentyl)-7-oxabicyclo[2.2.1]hept-2-yl]-5-heptenoic acid, methyl ester To a suspension of 686 mg of purified cuprous bromide (4.8 mmole) in 12 ml of dry THF, cooled at 0°-5° C. was added with stirring 1.35 ml of a 3.5M solution of red-Al (sodium bis(2-methoxyethoxy)aluminumhydride) in toluene dropwise. The solution was stirred at 0°-5° C. for 30 minutes, whereupon it was cooled to −78° C. and 2 ml of n-butanol (18 mmole) was added rapidly, followed by a solution of 476 mg of Example 1 Part A (3) enone (1.2 mmole) in 4 ml of dry THF. After 10 minutes at −78° C., the reaction mixture was warmed to −20° C. and left for an additional one hour. The reaction mixture was quenched by addition of 70 ml of water and then poured into saturated ammonium chloride solution and was extracted with ether (x3). The ether extract was dried over anhydrous magnesium sulfate, filtered and the filtrate was concentrated under reduced pressure. 480 Mg of desired title ketone was obtained (100% yield) as a colorless oil.

B.

[1S-[1α,2β(Z),3β(3R,4S),4α]]-7-[3-(3-Hydroxy-4-phenyl-1-pentyl)-7-oxabicyclo[2.2.1]hept-2-yl]-5-heptenoic acid, methyl ester To a solution of 400 mg of title A ketone (1 mmole) in 2 ml of methanol and 2 ml of dry THF is added with stirring 400 mg of ceric (III) chloride hydrate (1 mmole). After stirring at room temperature for 10 minutes, the reaction mixture is cooled to −50° C. and 40 mg of solid sodium borohydride (∼1 mmole) is added to the reaction mixture. The reaction mixture is stirred at −50° C. for 45 minutes, whereupon 5 ml of acetone is added to destroy excess of borohydride. The mixture is stirred for an additional 5 minutes at −50° C. The cooling bath is removed and the reaction mixture is evaporated to dryness. The crude residue is diluted with ether and washed with 1N aqueous hydrochloric acid solution. The ether extract is dried over anhydrous MgSO₄ and concentrated under reduced pressure. The crude residue is chromatographed on a silica gel column and eluted with 30–50% ethyl acetate in hexane to obtain the desired title 3R-alcohol.

C. [1α,2β(5Z),3β(3R,4S,4α]-2-[[4-[3-(3-Hydroxy-4-phenyl-1-pentyl)-7-oxabicyclo[2.2.1]hept-2-yl]-2-butenyl]oxy]ethano Following the procedure of Example 1 except substituting the Part B alcohol for the Example 1 Part A alcohol, the title compound is obtained.

EXAMPLE 22

[1α,2β(E),3β(3R,4S),4α]-2-[[4-[3-(3-Hydroxy-4-phenyl-1-pentyl)-7-oxabicyclo[2.2.1]hept-2-yl]-2-butenyl]oxy]ethanol Following the procedure of Example 21, Example 1 Parts A and B, except substituting the Example 21 Part B alcohol for the Example 1 Part A alcohol, the title compound is obtained.

EXAMPLE 23

[1S-[1α,2β(5Z),3β(4S),4α]]-2-[[4-[3-(3-Hydroxy-3-phenyl-1-propyl)-7-oxabicyclo[2.2.1]hept-2-yl]-2-butenyl]oxy]ethanol Following the procedure of Example 21 and Example 1 except substituting benzoic acid for 2-phenylpropionic acid, the title compound is obtained.

EXAMPLE 24

[1S-[1α,2β(5Z),3β(4S),4α]]-2-[[4-[3-(3-Hydroxy-4-phenyl-1-butyl)-7-oxabicyclo[2.2.1]hept-2-yl]-2-butenyl]oxy]ethanol Following the procedure of Example 21 and Example 1 except substituting phenylacetic acid for 2-phenylpropionic acid, the title compound is obtained.

EXAMPLE 25

[1S-[1α,2β(5Z),3β(4S),4α]]-2-[[4-[3-(3-Hydroxy-3-cyclohexyl-1-propyl)-7-oxabicyclo[2.2.1]hept-2-yl]2-butenyl]oxy]ethanol Following the procedure of Example 21 and Example 1 except substituting cyclohexylcarboxylic acid for 2-phenylpropionic acid, the title compound is obtained.

EXAMPLE 26

[1S-[1α,2β(5Z),3β(4S),4α]]-2-[[4-[3-(3-Hydroxy-4-cyclopentyl-1-butyl)-7-oxabicyclo[2.2.1]hept-2-yl]-2-butenyl]thio]ethanol Following the procedure of Examples 21 and 14 except substituting cyclopentylacetic acid for 2-phenylpropionic acid, the title compound is obtained.

EXAMPLE 27

[1S-[1α,2β(5Z),3β(4S),4α]]-2-[[4-[3-(3-Hydroxy-5-hexenyl)-7-oxabicyclo[2.2.1]hept-2-yl]-2-butenyl]thio]ethanol Following the procedure of Example 21 and Example 14 except substituting 2-propenyl carboxylic acid for 2-phenylpropionic acid, the title compound is obtained.

EXAMPLE 28

[1S-[1α,2β(5Z),3β(4S),4α]]-2-[[4-[3-(3-Hydroxy-1-nonyl)-7-oxabicyclo[2.2.1]hept-2-yl]-2-butenyl]thio]ethanol Following the procedure of Example 21 and Example 14 except substituting hexanecarboxylic acid for 2-phenylpropionic acid, the title compound is obtained.

EXAMPLE 29

[1S-[1α,2β(2E,5Z),3β(4S),4α]]-2-[[4-[3-(3-Hydroxy-3-phenyl-1-propyl)-7-oxabicyclo[2.2.1]hept-2-yl]-2-butenyl]thio]ethanol Following the procedure of Examples 21 and 14 except substituting benzoic acid for 2-phenylpropionic acid, the title compound is obtained.

EXAMPLE 30

[1S-[1α,2β(2E,5Z),3β(4S),4α]]-[[2-[[4-[3-(3-Hydroxy-4-phenyl-1-butyl)-7-oxabicyclo[2.2.1]hept-2-yl]-2-butenyl]thio]ethanol Following the procedure of Examples 21 and 14 except substituting phenylacetic acid for 2-phenylpropionic acid, the title compound is obtained.

EXAMPLES 31 TO 40

Following the procedure of Example 1 (where B is CH=CH and A is O), Example 20 (where B is $(CH_2)_2$ and A is O) or Example 14 (where B is CH=CH and A is S) or Examples 14 and 21 (where B is $(CH_2)_2$ and A is S), except substituting for 2-phenylpropionic acid, the compound shown in Column I of Table I set out below, substituting for carbomethoxymethylenetriphenylphosphorane, the compound shown in Column II and substituting for 1-[2-bromoethoxy]tetrahydropyran, the compound shown in Column III, the compound of the invention shown in Column IV is obtained.

TABLE I

| | Column I | Column II | Column III | |
|---|---|---|---|---|
| Ex. No. | $R^3$—COOCH$_3$ <br> $R^3$ | $(C_6H_5)_3P$=CH—$(CH_2)_{m-1}$—CH$_2$CH$_3$ <br> m | 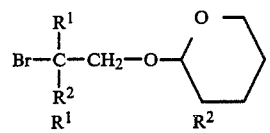 <br> $R^1$ | $R^2$ |
| 31. | CH$_3$ | 2 | H | CH$_3$ |
| 32. | C$_6$H$_5$ | 3 | C$_2$H$_5$ | CH$_3$ |
| 33. | C$_6$H$_5$CH$_2$ | 3 | C$_3$H$_7$ | H |
| 34. |  | 4 | CH$_3$ | CH$_3$ |
| 35. | 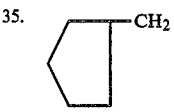 | 4 | H | H |
| 36. | CH$_3$—CH=CH— | 5 | CH$_3$ | H |
| 37. | C$_2$H$_5$ | 1 | CH$_3$ | CH$_3$ |
| 38. | C$_6$H$_4$(CH$_2$)$_2$ | 1 | C$_4$H$_9$ | H |

TABLE I-continued

| Ex. No. | | | | | |
|---|---|---|---|---|---|
| 39. | (cyclopentyl) | | 2 | H | CH₃ |
| 40. | CH₃CH₂—CH=CH— | | 3 | H | H |

Column IV $$\text{CH}_2-\text{CH}=\text{CH}-(\text{CH}_2)_m-\text{A}-\underset{R^2}{\overset{R^1}{\text{C}}}-\text{CH}_2\text{OH}$$

with B—CH—R³ / OH substituent on bicyclic system

| Ex. No. | B | m | A | R¹ | R² | R³ |
|---|---|---|---|---|---|---|
| 31. | CH=CH | 2 | S | H | CH₃ | CH₃ |
| 32. | (CH₂)₂ | 3 | O | C₂H₅ | CH₃ | C₆H₅ |
| 33. | CH=CH | 3 | S | C₃H₇ | H | C₆H₅CH₂ |
| 34. | (CH₂)₂ | 4 | O | CH₃ | CH₃ | cyclohexyl |
| 35. | CH=CH | 4 | S | H | H | cyclopentyl-CH₂ |
| 36. | (CH₂)₂ | 5 | O | CH₃ | H | CH₃—CH=CH— |
| 37. | CH=CH | 1 | S | CH₃ | CH₃ | C₂H₅ |
| 38. | (CH₂)₂ | 1 | O | C₄H₉ | H | C₆H₄(CH₂)₂ |
| 39. | CH=CH | 2 | S | H | CH₃ | cyclopentyl |
| 40. | (CH₂)₂ | 3 | O | H | H | CH₃CH₂—CH=CH— |

EXAMPLES 41 AND 42

[1S-[1α,2β(Z),3β(1E,3R,4S),4α]]-[[4-[3-(3-Hydroxy-3-phenyl-1-propenyl)-7-oxabicyclo[2.2.1]hept-2-yl]-2-butenyl]oxy]acetic acid, t-butyl ester (Example 41); and the free acid (Example 42)

Following the procedure of Examples 2 and 3 except substituting benzoic acid for 2-phenylpropionic acid, the title compound is obtained.

EXAMPLES 43 AND 44

[1S-[1α,2β(Z),3β(1E,3R,4S),4α]]-[[4-[3-(3-Hydroxy-4-phenyl-1-butenyl)-7-oxabicyclo[2.2.1]hept-2-yl]-2-butenyl]oxy]acetic acid, t-butyl ester (Example 43); and the free acid (Example 44)

Following the procedure of Examples 2 and 3 except substituting phenylacetic acid for 2-phenylpropionic acid, the title compound is obtained.

EXAMPLES 45 AND 46

[1S-[1α,2β(Z),3β(1E,3R,4S),4α]]-[[4-[3-(3-Hydroxy-3-cyclohexyl-1-propenyl)-7-oxabicyclo[2.2.1]hept-2-yl]-2-butenyl]oxy]acetic acid, t-butyl ester (Example 45); and the free acid (Example 46)

Following the procedure of Examples 2 and 3 except substituting cyclohexyl carboxylic acid for 2-phenylpropionic acid, the title compound is obtained.

EXAMPLES 47 AND 48

[1S-[1α,2β(Z),3β(1E,3R,4S),4α]]-[[4-[3-(3-Hydroxy-4-cyclopentyl-1-butenyl)-7-oxabicyclo[2.2.1]hept-2-yl]-2-butenyl]oxy]acetic acid, t-butyl ester (Example 47); and the free acid (Example 48)

Following the procedure of Examples 2 and 3 except substituting cyclopentylacetic acid for 2-phenylpropionic acid, the title compound is obtained.

EXAMPLES 49 AND 50

[1S-[1α,2β(Z),3β(1E,3R,4S),4α]]-[[4-[3-(3Hydroxy-1,5-hexadienyl)-7-oxabicyclo[2.2.1]hept-2-yl]-2-butenyl]oxy]acetic acid, t-butyl ester (Example 49); and the free acid (Example 50)

Following the procedure of Examples 2 and 3 except substituting 2-propenyl carboxylic acid for 2-phenylpropionic acid, the title compound is obtained.

EXAMPLES 51 AND 52

[1S-[1α,2β(Z),3β(1E,3R,4S),4α]]-[[4-[3-(3-Hydroxy-1-nonenyl-7-oxabicyclo[2.2.1]hept-2-yl]-2-butenyl]oxy]acetic acid, t-butyl ester (Example 51); and the free acid (Example 52)

Following the procedure of Examples 2 and 3 except substituting hexane carboxylic acid for 2-phenylpropionic acid, the title compound is obtained.

EXAMPLES 53 AND 54

[1S-[1α,2β(Z),3β(1E,3R,4S),4α]]-[[4-[3-(3-Hydroxy-1-pentenyl)-7-oxabicyclo[2.2.1]hept-2-yl]-2-butenyl]thio]acetic acid, methyl ester (Example 53); and the free acid (Example 54)

Following the procedure of Examples 14 and 3 except substituting propionic acid for 2-phenylpropionic acid, the title compound is obtained.

EXAMPLES 55 AND 56

[1S-[1α,2β(Z),3β(1E,3R,4S),4α]]-[[4-[3-(3-Hydroxy-3-phenyl-1-propenyl)-7-oxabicyclo[2.2.1]hept-2-yl]-2-butenyl]thio]acetic acid, methyl ester (Example 55); and the free acid (Example 56)

Following the procedure of Examples 14 and 3 except substituting benzoic acid for 2-phenylpropionic acid, the title compound is obtained.

EXAMPLES 57 AND 58

[1S-[1α,2β(Z),3β(1E,3R,4S),4α]]-[[4-[3-(3-Hydroxy-3-cyclohexyl-1-propenyl)-7-oxabicyclo[2.2.1]hept-2-yl]-2-butenyl]thio]acetic acid, methyl ester (Example 57); and the free acid (Example 58)

Following the procedure of Examples 14 and 3 except substituting cyclohexylcarboxylic acid for 2-phenylpropionic acid, the title compound is obtained.

EXAMPLES 59 AND 60

[1S-[1α,2β(Z),3β(1E,3R,4S),4α]]-[[4-[3-(3-Hydroxy-3-cycloheptyl-1-propenyl)-7-oxabicyclo[2.2.1]hept-2-yl]-2-butenyl]thio]acetic acid, methyl ester (Example 59); and the free acid (Example 60)

Following the procedure of Examples 14 and 3 except substituting cycloheptyl carboxylic acid for 2-phenylpropionic acid, the title compound is obtained.

EXAMPLES 61 AND 62

[1S-[1α, 2β(Z),3β(1E,3R,4S),4α]]-[[4-[3-(3-Hydroxy-4-cyclopentyl-1-butenyl)-7-oxabicyclo[2.2.1]hept-2-yl]-2-butenyl]thio]acetic acid, methyl ester (Example 61); and the free acid (Example 62)

Following the procedure of Examples 14 and 3 except substituting cyclopentylacetic acid for 2-phenylpropionic acid, the title compound is obtained.

EXAMPLES 63 AND 64

[1S-[1α, 2β(Z),3β(1E,3R,4S),4α]]-[[4-[3-(3-Hydroxy-1,6-heptadienyl)-7-oxabicyclo[2.2.1]hept-2-yl]-2-butenyl]thio]acetic acid, methyl ester (Example 63); and the free acid (Example 64)

Following the procedure of Examples 14 and 3 except substituting 3-butenyl carboxylic acid for 2-phenylpropionic acid, the title compound is obtained.

EXAMPLES 65 AND 66

[1S-[1α,2β(Z),3β(1E,3R,4S),4α]]-[[4-[3-(3-Hydroxy-1-hexenyl)-7-oxabicyclo[2.2.1]hept-2-yl]-2-butenyl]thio]acetic acid, methyl ester (Example 65); and the free acid (Example 66)

Following the procedure of Examples 14 and 3 except substituting propionic acid for 2-phenylpropionic acid, the title compound is obtained.

EXAMPLES 67 AND 68

[1α, 2β(E),3β(3R,4S),4α]-[[4-[3-(3-Hydroxy-4-phenyl-1-pentyl)-7-oxabicyclo[2.2.1]hept-2-yl]-2-butenyl]oxy]acetic acid, methyl ester (Example 67); and the free acid (Example 68)

Following the procedure of Example 21, Examples 2 and 3, except substituting the Example 16 Part B alcohol for the Example 1 Part A alcohol, the title compound is obtained.

EXAMPLES 69 AND 70

[1S-[1α,2β(E),3β(4S),4α]]-[[4-[3-(3-Hydroxy-3-phenyl-1-propyl)-7-oxabicyclo[2.2.1]hept-2-yl]-2-butenyl]oxy]acetic acid, methyl ester (Example 69); and the free acid (Example 70)

Following the procedure of Example 21 and Examples 2 and 3 except substituting benzoic acid for 2-phenylpropionic acid, the title compound is obtained.

EXAMPLES 71 AND 72

[1S-[1α, 2β(E),3β(4S),4α]]-[[4-[3-(3-Hydroxy-4-phenyl-1-butyl)-7-oxabicyclo[2.2.1]hept-2-yl]-2-butenyl]oxy]acetic acid, methyl ester (Example 71); and the free acid (Example 72)

Following the procedure of Example 21 and Examples 2 and 3 except substituting phenylacetic acid for 2-phenylpropionic acid, the title compound is obtained.

EXAMPLES 73 AND 74

[1S-[1α,2β(E),3β(4S),4α]]-7-[3-(3-Hydroxy-3-cyclohexyl-1-propyl)-[[4-oxabicyclo[2.2.1]hept-2-yl]-2-butenyl]oxy]acetic acid, methyl ester (Example 73); and the free acid (Example 74)

Following the procedure of Example 21 and Examples 2 and 3 except substituting cyclohexylcarboxylic acid for 2-phenylpropionic acid, the title compound is obtained.

EXAMPLES 75 AND 76

[1S-[1α,2β(E),3β(4S),4α]]-[[4-[3-(3-Hydroxy-4-cyclopentyl-1-butyl)-7-oxabicyclo[2.2.1]hept-2-yl]-2-butenyl]thio]acetic acid, methyl ester (Example 75); and the free acid (Example 76)

Following the procedure of Examples 21 and 14 and Examples 2 and 3 except substituting cyclopentylacetic acid for 2-phenylpropionic acid, the title compound is obtained.

EXAMPLES 77 AND 78

[1S-[1α,2β(E),3β(4S),4α]]-[[4-[3-(3-Hydroxy-5-hexenyl)-7-oxabicyclo[2.2.1]hept-2-yl]-2-butenyl]thio]acetic acid, methyl ester (Example 77); and the free acid (Example 78)

Following the procedure of Examples 21 and 14 and Examples 2 and 3 except substituting 2-propenyl carboxylic acid for 2-phenylpropionic acid, the title compound is obtained.

EXAMPLES 79 AND 80

[1S-[1α,2β(E),3β(4S),4α]]-[[4-[3-(3-Hydroxy-1-nonyl)-7-oxabicyclo[2.2.1]hept-2-yl]-2-butenyl]thio]acetic acid, methyl ester (Example 79); and the free acid (Example 80)

Following the procedure of Examples 21 and 14 and Examples 2 and 3 except substituting hexanecarboxylic acid for 2-phenylpropionic acid, the title compound is obtained.

EXAMPLES 81 TO 90

Following the procedure of Examples 2 and 3 (where B is CH=CH and A is O), Examples 6 and 3 (where B is CH=CH and A is S), Examples 21, 2 and 3 (where B is $(CH_2)_2$ and A is O) and Examples 21, 14, 2 and 3 (where B is $(CH_2)_2$ and A is S), except substituting for 2-phenylpropionic acid, the compound shown in Column I of Table II set out below, substituting for carbomethoxymethylenetriphenylphosphorane, the compound shown in Column II, and substituting for 1-[2-bromoethoxy]tetrahydropyran, the compound shown in Column III, the compound of the invention shown in Column IV is obtained.

TABLE II

| Ex. No. | Column I<br>$R^3$—COOCH$_3$<br>$R^3$ | Column II<br>$(C_6H_5)_3P$=CH—$(CH_2)_{m-1}$—CO$_2$CH$_3$<br>m | Column III<br>Br—C(R$^1$)(R$^2$)—CH$_2$—O—(tetrahydropyranyl)<br>$R^1$ | $R^2$ |
|---|---|---|---|---|
| 81. | CH$_3$ | 2 | H | CH$_3$ |
| 82. | C$_6$H$_5$ | 3 | C$_2$H$_5$ | CH$_3$ |
| 83. | C$_6$H$_5$CH$_2$ | 3 | C$_3$H$_7$ | H |
| 84. |  | 4 | CH$_3$ | CH$_3$ |
| 85. | —CH$_2$ | 4 | H | H |
| 86. | CH$_3$—CH=CH— | 5 | CH$_3$ | H |
| 87. | C$_2$H$_5$ | 1 | CH$_3$ | CH$_3$ |
| 88. | C$_6$H$_4$(CH$_2$)$_2$ | 1 | C$_4$H$_9$ | H |
| 89. |  | 2 | H | CH$_3$ |
| 90. | CH$_3$CH$_2$—CH=CH— | 3 | H | H |

Column IV

| Ex. No. | B | m | A | $R^1$ | $R^2$ | $R^3$ |
|---|---|---|---|---|---|---|
| 81. | CH=CH | 2 | S | H | CH$_3$ | CH$_3$ |
| 82. | (CH$_2$)$_2$ | 3 | O | C$_2$H$_5$ | CH$_3$ | C$_6$H$_5$ |
| 83. | CH=CH | 3 | S | C$_3$H$_7$ | H | C$_6$H$_5$CH$_2$ |

TABLE II-continued

| | | | | | | |
|---|---|---|---|---|---|---|
| 84. | (CH$_2$)$_2$ | 4 | O | CH$_3$ | CH$_3$ |  |
| 85. | CH=CH | 4 | S | H | H | 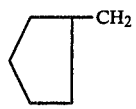 |
| 86. | (CH$_2$)$_2$ | 5 | O | CH$_3$ | H | CH$_3$—CH=CH— |
| 87. | CH=CH | 1 | S | CH$_3$ | CH$_3$ | C$_2$H$_5$ |
| 88. | (CH$_2$)$_2$ | 1 | O | C$_4$H$_9$ | H | C$_6$H$_4$(CH$_2$)$_2$ |
| 89. | CH=CH | 2 | S | H | CH$_3$ |  |
| 90. | (CH$_2$)$_2$ | 3 | O | H | H | CH$_3$CH$_2$—CH=CH— |

What is claimed is:

1. A compound having the structural formula

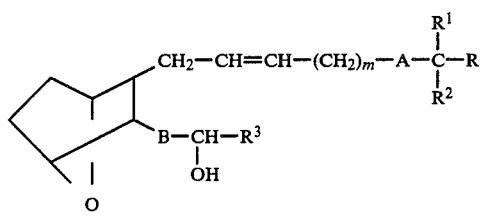

and including all stereoisomers thereof;

wherein A is sulfur or oxygen; m is 1 to 5; B is —CH=CH— or (CH$_2$)$_2$; R is —CH$_2$OH,

or CO$_2$H; R$^1$ and R$^2$ may be the same or different and are hydrogen or lower alkyl; and R$_3$ is lower alkyl, aryl, aralkyl, cycloalkyl, cycloalkylalkyl or lower alkenyl, wherein the term lower alkyl or alkyl by itself or as part of another group contains 1 to 12 carbons and is unsubstituted or substituted with halo, trifluoromethyl, alkoxy, aryl, alkyl-aryl, haloaryl, cycloalkyl or alkylcycloalkyl;

The term aryl by itself or as part of another group refers to monocyclic or bicyclic aromatic groups containing 6 to 10 carbons in the ring portion and is unsubstituted or substituted with 1 or 2 lower alkyl groups, 1 or 2 halogens and/or 1 or 2 lower alkoxy groups;

the term cycloalkyl by itself or as part of another group contains 3 to 12 carbons and is unsubstituted or substituted with 1 or 2 halogens, 1 or 2 lower alkyl groups and/or 1 or 2 lower alkoxy groups and;

the term lower alkenyl by itself or as part of another group contains from 2 to 12 carbons.

2. The compound as defined in claim 1 wherein A is O.

3. The compound as defined in claim 1 wherein A is S.

4. The compound as defined in claim 1 wherein B is —CH=CH—.

5. The compound as defined in claim 4 wherein R$^3$ is butyl, pentyl, hexyl, heptyl, 1,1-dimethylpentyl, or 2-phenylethyl.

6. The compound as defined in claim 1 having the name [1S-[1α, 2β(E),3β(1E,3R,4S),4α]]-2-[[4-[3-(3-hydroxy-4-phenyl-1-pentenyl)-7-oxabicyclo[2.2.1]hept-2-yl]-2-butenyl]oxy]ethanol, including all stereoisomers thereof.

7. The compound as defined in claim 1 having the name [1S-[1α, 2β,3β(1E,3R,4S),4α]]-4-[3-(3-hydroxy-4-phenyl-1-pentenyl)-7-oxabicyclo[2.2.1]hept-2-yl]-2-butenyl]oxy]acetic acid, including the methyl, ethyl or t-butyl esters thereof, and including all stereoisomers thereof.

8. The compound as defined in claim 1 having the name [1S-[1α, 2β(Z),3β(1E,3R,4S) ,4α]]-[[4-[3-(3-hydroxy-4-phenyl-1-pentenyl)-7-oxabicyclo[2.2.1]hept-2-yl]-2-butenyl]thio]acetic acid including the methyl ester thereof, and including all stereoisomers thereof.

9. A method of inhibiting platelet aggregation, inhibiting bronchoconstriction or treating peripheral vascular disease, which comprises administering to a mammalian host an effective amount of a compound as defined in claim 1 or a pharmaceutically acceptable salt thereof.

10. The method as defined in claim 9 wherein said compound is administered in an amount within the range of from about 1 to about 100 mg/kg.

* * * * *

UNITED STATES PATENT AND TRADEMARK OFFICE
CERTIFICATE OF CORRECTION

PATENT NO. : 4,591,603

DATED : May 27, 1986

INVENTOR(S) : Jagabandhu Das

It is certified that error appears in the above-identified patent and that said Letters Patent is hereby corrected as shown below:

Column 7, line 14 should read
   -- $\underline{A}$ $(C_6H_5)_3P=CH-(CH_2)_{m-1}-CO_2CH_3$ --.

Column 15, line 52, before "1α" insert --[--.
Column 18, line 48, delete "Q8".
Column 18, line 49, before "1S" insert --[--.
Column 20, line 29, "butenyl 9 oxy" should read
   --butenyl]oxy--.
Column 22, line 2, "[11α" should read --[1α--.

Signed and Sealed this

Twenty-third Day of December, 1986

Attest:

DONALD J. QUIGG

Attesting Officer          Commissioner of Patents and Trademarks